United States Patent [19]

Hozumi et al.

[11] Patent Number: 4,939,156
[45] Date of Patent: Jul. 3, 1990

[54] NEW TETRAMETHYL-CIS-DIAZA-BICYCLO{4.2.0}OCTANE-3,5-DIONE DERIVATIVES HAVING DIFFERENTIATION-INDUCING ACTIVITY AND ANTIVIRAL ACTIVITY

[75] Inventors: Motoo Hozumi, Ohmiya; Tsuneo Itoh, Tokyo; Yoshio Honma, Shobu; Norio Kawahara, Sapporo; Ichiro Ishikawa, Tokyo; Haruo Ogura, Matsudo, all of Japan

[73] Assignee: Meiji Seika Kaisha, Ltd., Japan

[21] Appl. No.: 219,200

[22] Filed: Jul. 8, 1988

[30] Foreign Application Priority Data

Jul. 11, 1987 [JP] Japan ................................. 62-172091
Mar. 9, 1988 [JP] Japan ................................. 63-53817

[51] Int. Cl.$^5$ .................. A61K 31/505; C07D 239/70
[52] U.S. Cl. ....................................... 514/258; 544/253; 536/23; 514/50; 204/157.72
[58] Field of Search .......................... 544/253; 514/258

[56] References Cited

U.S. PATENT DOCUMENTS 3,758,477  9/1973  Zeidler ................................. 544/253
4,542,219  9/1985  Hozumi et al. ....................... 546/22
4,703,110  10/1987 Shudo ................................... 534/566

FOREIGN PATENT DOCUMENTS 0163387 10/1982 Japan .
0199820 10/1985 Japan .
0076440 4/1986 Japan .

OTHER PUBLICATIONS

Breitman, et al., Proc. Natl. Acad. Sci. U.S.A., vol. 77, No. 5, pp. 2936–2940 (1980).
Pawson, et al., J. Medicinal Chemistry, vol. 25, No. 11, 1269–1277 (11/82).
Koeffler, Blood, The Journal of the American Society of Hematology, vol. 62, No. 4, pp. 709–721 (10/83).
Wexler, et al., J. Am. Chem. Soc., vol. 98(6), pp. 1602–1604 (03/17/76).
Wexler, et al., J. Org. Chem., vol. 49, No. 15, pp. 2733–2738 (1984).
Charlton, et al., Canadian J. Chem., vol. 54, pp. 1445–1448 (1976).
Honma, et al., Anticancer Res., vol. 8(4), pp. 695–699 (04/88).

*Primary Examiner*—Diana G. Rivers
*Attorney, Agent, or Firm*—Lalos & Keegan

[57] ABSTRACT

As new compounds are now provided 7,7,8,8,-tetramethyl-cis-diaza-bicyclo{4.2.0}octane-3,5,-dione derivatives which have an activity to induce the differentiation of tumor cells and are useful as antitumor agent, and which also have an antiviral activity against various viruses and are useful as antiviral agent. These new derivatives may be produced by a photo-addition reaction of a uracil compound with 2,3-dimethyl-2-butene.

6 Claims, No Drawings

NEW TETRAMETHYL-CIS-DIAZA-BICYCLO{4.2.0}OCTANE-3,5-DIONE DERIVATIVES HAVING DIFFERENTIATION-INDUCING ACTIVITY AND ANTIVIRAL ACTIVITY

SUMMARY OF THE INVENTION

This invention relates to new compounds which have an activity of inducing or stimulating the differentiation of animal's cells and thus have the activity of inducing decarcinogenesis of the tumor cells grown in an mammalian animal and are therefore useful as a antitumor agent, and which also have a antiviral activity against various kinds of viruses and hence are useful as an antiviral agent. More particularly, this invention relates to new 7,7,8,8-tetramethyl-cis-diaza-bicyclo{4.2.0}octane-3,5-dione derivatives which have the activity of inducing the differentiation of the animal's cells and also have the antiviral activity. This invention also relates to a process for the production of these new compounds, and this invention further relates to medicinal applications of these new compounds.

BACKGROUND OF THE INVENTION

Hithertobefore, different kinds of compounds having the differentiation-inducing activity have been studied. A method of making decarcinogenesis of the tumor cells by inducing the differentiation of the tumor cells has been proposed as described, for instance, in the "Proc. Natl. Acad. Sci. USA" 77, page 2936 (1980); the "J. Med. Chem." 25, page 1269 (1982); the "Blood" 62, page 709 (1983) and "THE RECINOIDS" Vol. 1-2, M. B. Sporn et al, Academic Press (1984). Further, for example, Japanese patent application first application "Kokai" No. 163387/82 (or its corresponding U.S. Pat. No. 4,542,219) discloses some ethylene glycol derivatives; Japanese patent application first publication "Kokai" No. 199820/85 discloses a substance OC-1 which is extracted from an earth worm, Oliochaeta; and Japanese patent application first publication "Kokai" No. 76440/86 discloses some derivatives of benzoic acid, and the respective compounds as disclosed in the afore-said three Japanese patent application first publications are all such antitumor compounds having the differentiation-inducing activities which stimulate the differentiation of the tumor cell and thus invoke the decarcinogenesis of the tumor cells.

We, the present inventors, have now made our investigations in an attempt to provide new compounds which have the differentiation-inducing activity, and to provide these new compounds as an antitumor agent.

DETAILED DESCRIPTIONS OF THE INVENTION

As a result of our investigations, we have succeeded in synthesizing a 7,7,8,8-tetramethyl-cis-diaza-bicyclo{4.2.0}octane-3,5-dione derivative represented by the general formula (I)

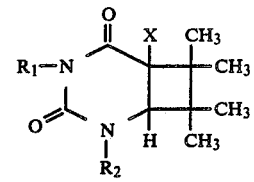

wherein $R_1$ denotes a hydrogen atom, a lower alkyl group, an aryl group or an aralkyl group and $R_2$ denotes a hydrogen atom, a lower alkyl group, an aryl group, an aralkyl group or 2',3'-isopropylidene-ribofiranosyl group, and X denotes a hydrogen or fluorine atom, as new compounds. Furthermore, we have now found that the new compounds of the general formula (I) exhibit the differentiation-inducing activity that stimulates the differentiation (decarcinogenesis) of the tumor cells. Besides, we have now discovered that the new compounds of the general formula (I) exhibit also the antiviral activity.

According to a first aspect of this invention, therefore, there is provided a compound of the general formula (I)

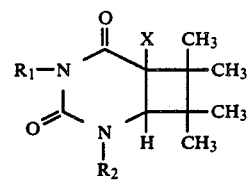

wherein $R_1$ denotes a hydrogen atom, a lower alkyl group, an aryl group or an aralkyl group and $R_2$ denotes a hydrogen atom, a lower alkyl group, an aryl group, an aralkyl group or 2',3'-isopropylidene-ribofuranosyl group, and X denotes a hydrogen or fluorine atom.

According to a first preferred embodiment of the first aspect of this invention, there is provided a compound of the formula (Ia)

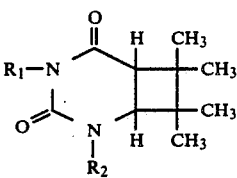

wherein $R_1$ is a hydrogen atom or a lower alkyl group and $R_2$ is a lower alkyl group or 2,3-isopropylidene group.

According to the second preferred embodiment, there is provided a compound of the formula (Ib)

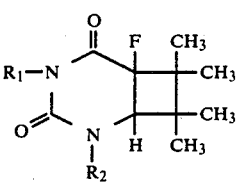

wherein $R_1$ is a hydrogen atom, a lower alkyl group, an aryl group or an aralkyl group and $R_2$ is a hydrogen atom, a lower alkyl group, an aryl group or an aralkyl group.

In the compounds of the general formula (I) and of the formula (Ia) or (Ib), $R_1$ and $R_2$ each may be a lower alkyl group, and then the lower alkyl group may be an alkyl group of 1 to 6 carbon atoms, especially an alkyl group of 1 to 4 carbon atoms, such as methyl, ethyl, n-propyl, iso-propyl, n-butyl, iso-butyl, tert-butyl, n-pentyl, iso-pentyl, n-hexyl and iso-hexyl groups. Preferred examples of the alkyl group include methyl and ethyl groups. A typical example of an aryl group is a phenyl group, unsubstituted or substituted e.g. with a lower alkyl group such as methyl and ethyl. A typical example of an aralkyl group is a benzyl group, unsubstituted or substituted with a lower alkyl group such as methyl and ethyl. Particularly, the aralkyl group may be a phenyl-($C_1$–$C_4$)alkyl group, for example, benzyl or phenethyl group.

Particular examples of the compound of the formula (Ia) include 2,4,7,7,8,8-hexamethyl-cis-2,4-diaza-bicyclo{4.2.0}octane-3,5-dione; 2,4-diethyl-7,7,8,8-tetramethyl-cis-2,4-diaza-bicyclo{4.2.0}octane-3,5-dione; and 7,7,8,8-tetramethyl-2-(2′,3′-isopropylidene-ribofuranosyl)-cis-2,4-diaza-bicyclo{4.2.0}octane-3,5-dione.

Particular examples of the compound of the formula (Ib) include 6-fluoro-4,7,7,8,8-pentamethyl-2,4-diaza-bicyclo{4.2.0}octane-3,5-dione; 2-ethyl-6-fluoro-7,7,8,8-tetramethyl-2,4-diaza-bicyclo{4.2.0}octane-3,5-dione; 2,4-diethyl-6-fluoro-7,7,8,8-tetramethyl-2,4-diaza-bicyclo{4.2.0}octane-3,5-dione; and 2,4-dibenzyl-6-fluoro-7,7,8,8-tetramethyl-2,4-diaza-bicyclo{4.2.0}octane-3,5-dione.

According to the second aspect of this invention, there is provided a process for the production of the compound of the general formula (I) above, which comprises reacting an uracil compound of the formula (II)

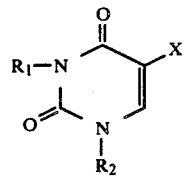

(II)

wherein $R_1$, $R_2$ and X are each as defined above, with 2,3-dimethyl-2-butene in an inert organic solvent under anhydrous conditions and under irradiation with light at a temperature of 0° C. to 40° C. to form the compound of the formula (I).

The reaction of the uracil compound of the formula (II) with 2,3-dimethyl-2-butene, namely tetramethylethylene may principally be achieved according to a photo-addition reaction in such a manner as described fully, for example, in the "Journal of Organic Chemistry" 49, page 2733 (1984).

In the process of this invention, the photo-addition reaction may preferably be carried out by reacting one molar proportion of the compound of the formula (II) with 1 molar proportion to a few tens molar proportion of 2,3-dimethyl-2-butene (most suitably at a molar ratio ranging from 1:10 to 1:12) in solution in an inert organic solvent and under anhydrous conditions. The organic solvent available for this purpose may preferably be dry acetone, dry benzene, dry hexane, dry petroleum ether, dry dioxane and the like. When the solution containing the compound (II) and 2,3-dimethyl-2-butene dissolved in a suitable dry organic solvent is irradiated with light-rays from a high-pressure mercury lamp, preferably under ice-cooling, the desired photo-addition reaction takes place, affording the compound of the formula (I). The reaction may be effected for 12 to 96 hours and at a temperature of 0° C. to 40° C., preferably at ambient temperature. The reaction may preferably be effected under an atmosphere of nitrogen gas and other unreactive gas. After the completed reaction, the reaction solution may be distilled to remove the solvent therefrom, and the residue may be purified by a preparative thin layer chromatography or a column chromatography on silica gel using a suitable development solvent so that the desired compound of the formula (I) is isolated and recovered.

The production of the compound of the formula (I) according to this invention is now illustrated with reference to the following Examples.

EXAMPLE 1

Production of 2,4,7,7,8,8-hexamethyl-cis-2,4-diaza-bicyclo{4.2.0}octane-3,5-dione (TI-27 Substance)

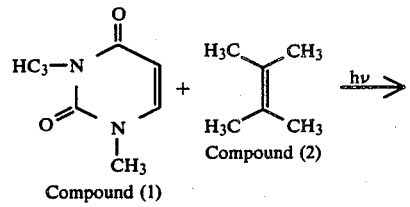

1,3-Dimethyluracil {Compound (1)}(426 mg; 3 mmol) and 2,3-dimethyl-2-butene, namely tetramethylethylene {Compound (2)}(2.50 g; 30 mmol) were dissolved in 550 ml of dry acetone, and the resulting solution, under the atmosphere of nitrogen gas and under ice-cooling, was irradiated with light from a high-pressure mercury lamp (400 Watts) via a pyrex-glass filter for 48 hours. The reaction solution obtained was distilled to remove the solvent therefrom, and then the residue was subjected to a preparative thin layer chromatography on silica gel using 3% methanol-chloroform as the development solvent. Such fractions of the eluate containing the above titled compound were combined and concentrated to dryness under reduced pressure to give 513 mg of the titled compound as a white needle-like crystal. Yield 76.3%. mp. 69°–70° C.

Mass spectrum m/z; 224($M^+$)

$^1$H-NMR(CDCl$_3$)δ: 0.93, 0.97, 1.12, 1.23 (each 3H, s, —CH$_3$×4), 2.93, 3.20 (each 3H, s, N—CH$_3$), 2.98 3.58 (each 1H, d, J=9.60 Hz, C$_1$H—C$_6$H)

EXAMPLE 2

Production of 2,4-diethyl-7,7,8,8-tetramethyl-cis-2,4-diaza-bicyclo{4.2.0}octane-3,5-dione (TI-16 Substance)

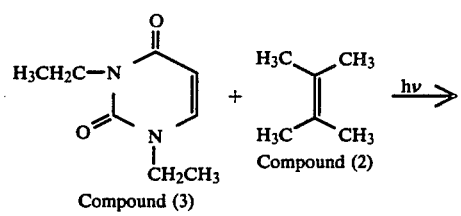

Compound (3)    Compound (2)

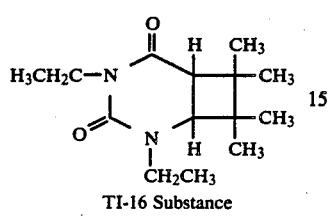

TI-16 Substance 1,3-Diethyluracil {Compound (3)}(1.10 g; 6.5 mmol) and 2,3-dimethyl-2-butene, namely tetramethylethylene {Compound (2)}(5.50 g; 65 mmol) were dissolved in 550 ml of dry acetone. The resulting solution was irradiated with the light in the same manner as in Example 1 to effect the photo-addition reaction, and the reaction solution was then processed in the same manner as in Example 1. The titled compound desired was obtained as a colorless and transparent oil in a yield of 917 mg (56.0%).

Mass spectrum m/z: 252(M+)

$^1$H-NMR(CDCl$_3$)δ: 0.93, 0.96, 1.09, 1.25 (each 3H, s, C—CH$_3$×4), 1.15, 1.21 (each 3H, t, CH$_2$CH$_3$), 2.93, 3.67 (each 1H, d, J=10.2 Hz), 3.92 (2H×2, d, CH$_2$CH$_3$×2).

Elemental Analysis

Found: C 66.09, H 9.47, N 11.09%; Calculated (for C$_{14}$H$_{24}$N$_2$O$_2$): C 66.63, H 9.59, N 11.10%

EXAMPLE 3

Production of 7,7,8,8-tetramethyl-2-(2′,3′-isopropylidene-ribofuranosyl)-cis-2,4-diaza-bicyclo{4.2.0}octane-3,5-dione (TI-28 Substance)

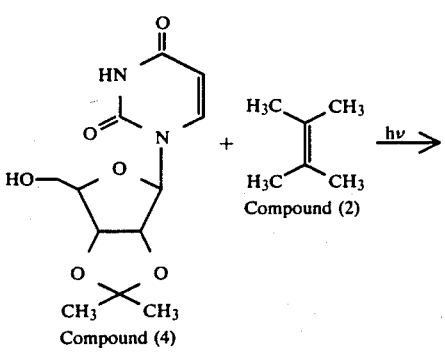

Compound (4)

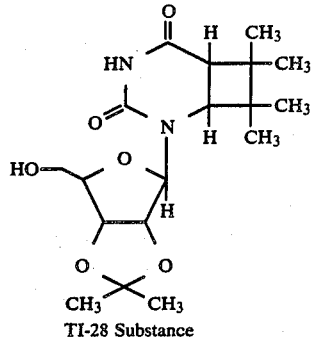

TI-28 Substance

2′,3′-Isopropylideneuridine {Compound (4)}(1.5 g; 5.28 mmol) and 2,3-dimethyl-2-butene, namely tetramethylethylene {Compound (2)}(4.40 g; 52.8 mmol) were dissolved in 550 ml of dry acetone. The resulting solution was irradiated with the light in the same manner as in Example 1 to effect the reaction, and the reaction solution was then processed in the same manner as in Example 1. The titled compound was afforded as a colorless crystals in a yield of 1168 mg (60.1%). mp. 97°–99° C.

Mass spectrum m/z: 353(M$^{30}$—CH$_3$), $^1$H-NMR(CDCl$_3$)δ: 1.03, 1.12, 1.26 (each 3H, s, isopropylidene), 2.91. 3.90 (each 1H, d, J=9.6 Hz=CH—CH=), 3.33–3.66 (2H, m, —CH$_2$—), 4.20 (1H, dd, J$_{34}$=3.3 Hz, J$_{45a}$=6.3Hz), 4.87 (1H, J$_{12}$=3.0 Hz C′-1), 4.98 (1H, dd, J$_{34}$=3.3 Hz, J$_{23}$=6.6 Hz, C′-3), 5.12 (1H, dd, J$_{12}$=3.0 Hz, J$_{23}$=6.6 Hz, C′-2).

EXAMPLE 4

Production of 6-fluoro-4,7,7,8,8-pentamethyl-2,4-diaza-bicyclo{4.2.0}octane-3,5-dione (TI-61 Substance)

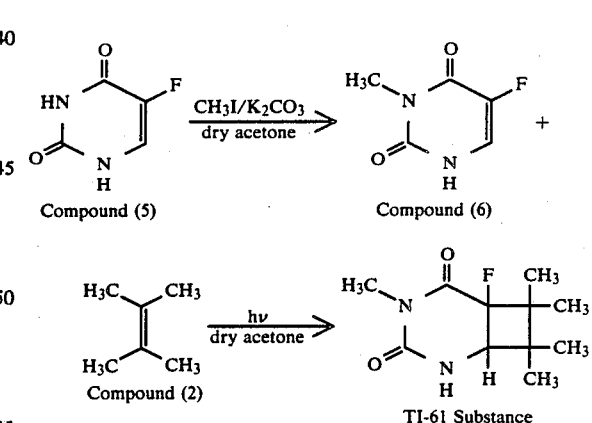

TI-61 Substance (a) 5-Fluorouracil, namely Compound (5) (1.30 g; 10 mmol), methyl iodide (CH$_3$I) (2.13 g; 15 mmol) and potassium carbonate (0.69 g; 5 mmol) were added to acetone (20 ml), and the resulting mixture was stirred at 60°–70° C. for 24 hours. The reaction solution obtained was filtered to remove potassium carbonate, and the filtrate was concentrated under reduced pressure. To the resulting residue was added a small volume of chloroform, and then the residue was fractionated by column chromatography on silica gel (eluent: chloroform) to isolate 5-fluoro-3-methyluracil, namely Compound (6) shown above (355 mg) as white needle-like crystals.

Compound (6):

Yield: 12%
Mass spectrum m/z: 144 (M+)
mp. 170°–171° C.
¹H-NMR(DMSO-d₆)
δ: 3.21 (3H, s, NCH₃); 7.76 (1H, d, 6-H, J=5.7 Hz); 11.02 (1H, b, NH)

Elemental Analysis

Calculated(for C₅H₅N₂O₂F): C 41.67, H 3.47, N 19.44%; Found: C 41.42, H 3.52, N 19.24%

(b) Compound (6)(216 mg; 1.5 mmol) as prepared in the above step (a) and 2,3-dimethyl-2-butene, namely Compound (2)(1.26 g; 15 mmol) were dissolved in acetone (600 ml). The resulting solution was irradiated with the light from a high-pressure mercury lamp (400 Watts) via a Vycol-filter for 72 hours under the atmosphere of nitrogen gas. The reaction solution obtained was concentrated under reduced pressure, and to the resulting residue was added a small volume of chloroform, and then the residue was purified by column chromatography on silica gel (eluent: chloroform-ethanol(10:1)) to give 340 mg of the titled TI-61 Substance as pale yellow needle-like crystals.

TI-61 Substance:

Yield: 99%
Mass spectrum m/z: 228 (M+)
mp. 123°–124° C.
¹H-NMR(CDCl₃)
δ: 0.87, 1.10, 1.12 (each 3H, s, CCH₃); 1.20 (3H, d, CCH₃, J=3.9 Hz); 3.21 (3H, s, NCH₃)

EXAMPLE 5

Production of 2-ethyl-6-fluoro-7,7,8,8-tetramethyl-2,4-diaza-bicyclo{4.3.0}octane-3,5-dione (TI-62 Substance)

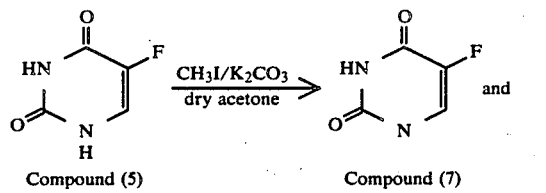

Compound (5) → Compound (7)

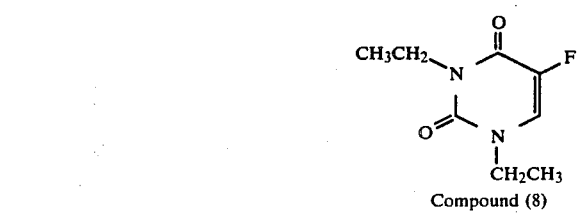

Compound (8)

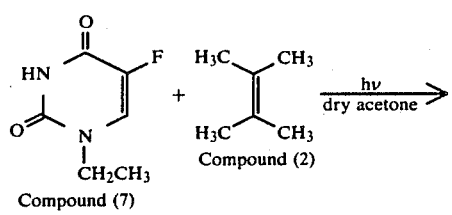

Compound (7) + Compound (2)

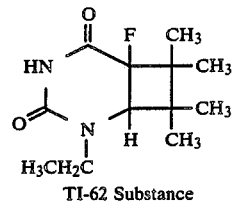

TI-62 Substance (a) 5-fluorouracil, namely Compound (5), (1.30 g; 10 mmol), ethyl iodide (2.34 g; 15 mmol) and potassium carbonate (0.69 g; 5 mmol) were added to acetone (20 ml). The resulting mixture was processed in the same manner as in Example 4 (a) to isolate 1-ethyl-5-fluorouracil, namely Compound (7) (316 mg), and 1,3-diethyl-5-fluorouracil, namely Compound (8) (232 mg), respectively, as white-colored needles.

Compound (7):

Yield: 20%
Mass spectrum m/z: 158 (M+)
mp. 183°–184° C.
¹H-NMR(DMSO-d₆)
δ: 1.15 (3H, t, CH₂CH₃, J=7.2 Hz), 3.64 (2H, q, CH₂CH₃, J=7.2 Hz), 8.07 (1H, d, 6-H, J=6.3 Hz), 11.67 (1H, b, NH)

Elemental Analysis

Calculated (for C₆H₇N₂O₂F): C 45.57, H 4.43, N 17.72%; Found: C 45.58, H 4.46, N 17.62%

Compound (8):

Yield: 13%
Mass spectrum m/z: 186(M+)
mp. 66°–68° C.
¹H-NMR(CDCl₃)
δ: 1.20, 1.29 (each 3H, t, CH₂CH₃, J=7.2 Hz), 3.77, 4.00 (each 2H, q, CH₂CH₃, J=7.2 Hz), 7.23 (1H, d, 6-H, J=5.7 Hz)

Elemental Analysis

Calculated (for C₈H₁₁N₂O₂F): C 51.61, H 5.91, N 15.05%; Found: C 51.50, H 6.15, N 14.99%

(b) Compound (7) (316 mg; 2 mmol) as prepared in the above step (a) and Compound (2), namely 2,3-dimethyl-2-butene (1.68 g; 20 mmol) were dissolved in acetone (600 ml). The resulting solution was irradiated with the light from a high-pressure mercury lamp (400 Watts) via a Vycol-filter for 72 hours under the atmosphere of nitrogen gas. The reaction solution obtained was concentrated under reduced pressure, and to the resulting residue was added a small volume of chloroform and then the residue was purified by column chromatography on silica gel {eluent: chloroform-ethanol (10:1)} to give the titled TI-62 Substance (200 mg) as a pale yellow oil.

TI-62 Substance:

Yield: 41%
Mass spectrum: 242 (M+)
¹H-NMR(CDCl₃)
δ: 0.82, 1.00, 1.14, 1.18 (each 3H, s, CCH₃), 1.14 (3H, t, CH₂CH₃, J=7.2 Hz), 3.91 (2H, q CH₂CH₃, J=7.2 Hz), 3.75 (1H, d, >CH—CF<, J=22.8 Hz), 8.43 (1H, b, NH)

Elemental Analysis

Calculated (for C₁₂H₁₉N₂O₂F): C 59.50, H 7.85, N 11.57%, Found: C 59.60, H 7.79, N 11.32%

EXAMPLE 6

Production of 2,4-diethyl-6-fluoro-7,7,8,8-tetramethyl-2,4-diaza-bicyclo{4.2.0}octane-3,5-dione (TI-65 Substance)

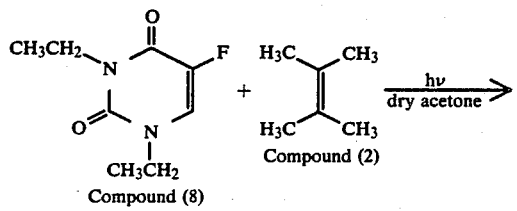

Compound (8) (186 mg; 1 mmol) as prepared in Example 5 (a) and Compound (2) (0.84 g; 1 mmol) were dissolved in acetone (600 ml). The resulting solution was irradiated with the light of a high-pressure mercury lamp (400 Watts) via a Vycol-filter for 72 hours under the atmosphere of nitrogen gas. The reaction solution obtained was concentrated under reduced pressure, and to the resulting residue was added a small volume of chloroform, and then the residue was purified by column chromatography on silica gel{chloroform-ethanol (10:1)} to give the titled TI-65 Substance (218 mg) as a lightly red oil.

TI-65 Substance:

Yield: 81%
Mass spectrum m/z: 270 (M⁺)
¹H-NMR(CDCl₃)
δ: 0.82, 1.01, 1.18 (each 3H, s, CCH₃), 1.25 (3H, d, CCH₃, J=3.9 Hz), 1.15 (3H, m, CH₂CH₃), 1.23 (3H, t, CH₂CH₃, J=7.2 Hz), 3.07, 3.68 (each 1H, m, CH₂CH₃), 3.72 (1H, d, >CH—CF<, J=22.8 Hz), 3.92 (2H, q, CH₂CH₃, J=7.2 Hz)

Elemental Analysis

Calculated (for C₁₄H₂₃N₂O₂F): C 62.22, H 8.52, N 10.37%; Found: C 62.18, H 8.79, N 10.60%

EXAMPLE 7

Production of 2,4-dibenzyl-6-fluoro-7,7,8,8-tetramethyl-2,4-diaza-bicyclo{4.2.0}octane-3,5-dione (TI-66 Substance)

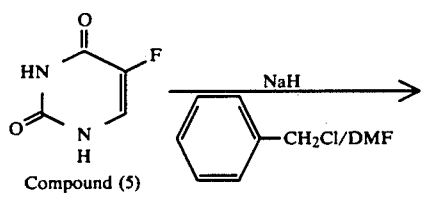

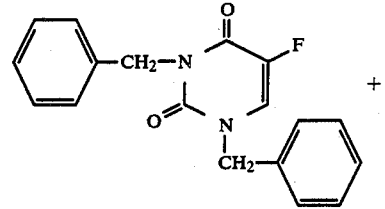

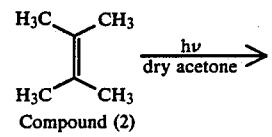

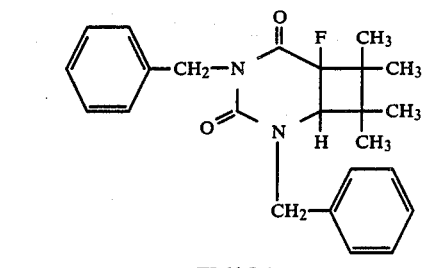

(a) 5-Fluorouracil, namely Compound (5) (1.30 g; 10 mmol) was dissolved in N,N-dimethylformamide (DMF) (20 ml), and the resulting solution was added with 60% sodium hydride (1.2 g; 30 mmol), and then the resulting mixture was stirred at 40°–50° C. for one hour. After the generation of hydrogen gas was ended, the reaction mixture was added with benzyl chloride (3.82 g; 30 mmol), and the mixture was stirred at 50°–60° C. for 2 hours. To the resultant reaction solution was added a 4% aqueous solution of sodium hydroxide (20 ml), the mixture was extracted with benzene (30 ml×3). The extracts were combined and dried over anhydrous sulfate, and then the solvent was distilled off under reduced pressure. The resulting residue was recrystallized from benzene-hexane (1:1) to give Compound (9) (2.22 g) as white needle-like crystals.

Compound (9):

Yield: 72%
Mass spectrum m/z: 310 (M⁺)
mp. 148°–149° C.
¹H-NMR(CDCl₃)
δ: 4.35 (2H, s, CH₂C₆H₅), 4.88, 5.15 (each 1H, s, CH₂C₆H₅), 7.15 (1H, d, 6-H, J=5.4 Hz), 7.20–7.57 (10H, m, CH₂C₆H₅×2)

Elemental Analysis

Calculated (for C₁₈H₁₅N₂O₂F): C 69.68, H 4.84, N 9.03%; Found: C 69.57, H 4.88, N 9.28%

(b) Compound (9) (2.00 g; 6.5 mmol) as prepared in the above step (a) and Compound (2) (5.46 g; 65 mmol) were dissolved in acetone (600 ml). The resulting solution was irradiated with the light in the same manner as in Example 4 to effect the reaction, and the reaction solution was then processed in the same manner as in Example 4 to give the titled TI-66 Substance (2.37 g) as white needle-like crystals.

TI-66 Substance:

Yield: 93%
Mass spectrum m/z: 394 (M+)
mp. 98°-100° C.
$^1$H-NMR(CDCl$_3$)
δ: 0.58, 0.87, 0.91 (each 3H, s, CCH$_3$), 1.11 (3H, d, CCH$_3$, J=3.9 Hz), 3.68 (1H, d, >CH—CF<, J=22.8 Hz), 4.11, 5.01 (each 1H, d, CH$_2$C$_6$H$_5$, J=14.4 Hz), 5.09 (2H, s, CH$_2$C$_6$H$_5$), 7.15-7.56 (1OH, m, C$_6$H$_5$×2)

Elemental Analysis

Calculated (for C$_{24}$H$_{27}$N$_2$O$_2$F): C 73.10, H 6.85, N 7.11%; Found: C 72.98, H 7.03, N 6.92%

As described hereinbefore, the compound of the general formula (I) according to this invention can exhibit the antitumor activity owing to the differentiation-inducing activity that stimulates the decarcinogenesis of the tumor cells. Besides, the compound of this invention can also exhibit the antiviral activity. According to another aspect of this invention, therefore, there is provided an antitumor composition comprising a compound of the formula (I) as the active ingredient, in association with a pharmaceutically acceptable liquid or solid carrier for the active ingredient, said compound of the formula (I) being present in an amount effective to treat inhibitingly the growth of tumor cells.

According to a further aspect of this invention, there is provided an antiviral composition comprising a compound of the formula (I) as the active ingredient, in association with a pharmaceutically acceptable liquid or solid carrier for the active ingredient, said compound of the formula (I) being present in an amount effective to treat inhibitingly the growth of virus.

Thus, the active compound of the formula (I) according to this invention is sparingly soluble in water and may be formulated into the form of pharmaceutical compositions with one or more pharmaceutically acceptable carriers or excipients. Examples of such carriers may be organic and inorganic inert carrier materials suitable for oral and parenteral administrations such as water, ethanol, gelatine, lactose, starch, magnesium stearate, talc, vegetable oil, acasia gum, polyalkyleneglycol and yellow soft paraffin. The pharmaceutical compositions may be in the form of solid formulations such as tablet, sugar-coated tablet, suppository and capsule or in the form of liquid formulations such as solution, suspension, and emulsion. The pharmaceutical compositions may be in sterile state and may contain a conventional adjuvant such as preservatives, stabilizers, wetting agent or emulsifying agents, isotonizers and buffering agents. The pharmaceutical composition according to this invention may also be in the form of ointment for tropical administration.

When the new compound of the formula (I) according to this invention is administered to patients in practice, it may normally be given through oral or nonoral routes. The new compound of this invention may be formulated into known preparations such as tablet and syrup for oral administration by mixing with conventional excipients as known in the pharmaceutical field so that it is given orally.

For the administration of the new compound of this invention to animals, the compound may also be formulated into an injectable solution or suspension suitable for intraperitoneal injection, subcutaneous injection, blood vessel injection, either intravenous or intra-arterial, and local injection. For the administration to human, the new compound of this invention may be formulated into injectable preparations suitable for blood vessel injection, either intravenous or intra-arterial, and local injection.

The dosage of the new compound of this invention may be decided in account of the results of animal tests and various factors, and the compound of this invention may be administered in dosage units continuously or intermittently so that the total dosages do not exceed a given value. Of course, however, the amount of the compound of this invention as administered may be changed appropriately with taking into account the administration route; conditions of patients or animals to be treated, such as age, body weight, sex, sensitivity, foods, time, duration, and way of administration; and symptoms of diseases. Only for a guideline, a normal dosage of the new compound of this invention upon use as an antitumor agent may be in a range of 0.1 mg/kg to 100 mg/kg, preferably of 0.5 mg/kg to 50 mg/kg, per unit dose a day. Optimum dosage and optimum numbers of administration of the compound of this invention are necessary to be decided by the medicinal experts through preliminary tests for determination of optimum dosage in view of the abovementioned guideline.

The pharmacological properties of the new compound of this invention are now described with reference to the following test.

Test 1

The experiments for estimating the cell differentiation-inducing activity of the new compounds of this invention that stimulates the differentiation or decarcinogenesis of tumor cells were conducted by a test wherein such concentration of the compound of this invention which can make 50% inhibition of the cell propagation of human premyelocytic leukemia cells (HL-60), namely the "IC$_{50}$" concentration of the compound 50% inhibitory against the cell propagation of the undifferentiated HL-60 cells was evaluated, and also by another test wherein it was estimated whether some of the HL-60 cells, after their treatment with the compound of this invention, have been differentiated and hence have gained the ability to reduce nitrobluetetrazolium (NBT). The human premyelocytic elukemia cells (HL-60 cell) are characterized by the ability to respond to pharmacological inducers of differentiation and can produce the normal granulocytes when they have been differentiated, as described in the "Blood" Vol. 54, No. 3, 713-733 (1979).

Thus, firstly the cell differentiation-inducing activity of the compound was assayed by the following procedure described in said "Blood". Namely, HL-60 cells were incubated by passing successively through RPMI 1640 media supplemented with 10% FCS (fetal calf serum), followed by adding the test compound at varying concentrations to aliquots of the culture of the HL-60 cells at the logarithmic phase of growth. The HL-60 cells thus incubated were further incubated in the presence of the test compound for 6 days and subsequently fixed to slide glasses. The fixed HL-60 cells were stained with May-Gruenwald-Giemsa's reagent and the morphology of the nuclei in the stained cells was examined to judge which of the cells has been differentiated into the normal granulocytes. Then, the number of the HL-60 cells which had propagated were counted.

As said "IC$_{50}$" concentration of the test compound was assumed such concentration of the test compound at which the counted number of the HL-60 cells having propagated was reduced by 50%, as compared to that counted in the control tests where the test compound was not used. The test results obtained are summarized in Table 1 below.

Secondly, the another aliquot of the culture of the HL-60 cells which were incubated in the above procedure in the presence of the test compound at its evaluated "$IC_{50}$" concentration was centrifuged to collect the cells, which were then diluted with a volume of RPMI 1640 medium supplemented with 10% FCS, to provide a given concentration of the cells. Subsequently, the cells which were diluted with said medium were added and mixed with 0.1% of NBT and then incubated at 37° C. for 20 minutes. The number of the cells which stained black color owing to the involved reduction of NBT and which could be judged to have the ability to reduce NBT was counted. Per cent of the counted number of the cells which showed the NBT-reducing ability was calculated based on the total number of the cells which were subjected to the treatment with NBT. The test results obtained here are also shown in Table 1 below.

TABLE 1

Effects on human premyelocytic leukemia cells HL-60

| Test Compound (Example No.) | Activity of test compound to inhibit by 50% the undifferetiated propagation of HL-60 cells (in term of "$IC_{50}$"; μg/ml) | Percent of the number of the cells showing the NBT-reducing ability after treatment with test compound at "$IC_{50}$" concentration |
|---|---|---|
| TI-27 substance (Example 1) | 35 | 51 |
| TI-16 substance (Example 2) | 17 | 69 |
| TI-28 substance (Example 3) | 62.5 | 37 |
| TI-61 substance (Example 4) | 39 | 18 |
| TI-62 substance (Example 5) | 9 | 34 |
| TI-65 substance (Example 6) | 36 | 20 |
| TI-66 substance (Example 7) | 7 | 65 |

As shown in the above test, the compounds of this invention exhibit a high activity to induce the differentiation of tumor cells and hence the effect of making decarcinogenesis of the cancer cells and are of a low toxicity to mammalian animals, so that they are promising to be useful as an excellent, chemotherapeutic antitumor agent.

Test 2

The tests here are to demonstrate the antiviral activity of the compound of this invention against a variety of viruses.

(a) Cytotoxicity of the compounds of this invention against the test animal cells which were used for incubation of viruses was at first evaluated by determining the minimum concentrations (μg/ml) of the compounds which can denature the test cells. For the test animal cells to which the virus to be tested was inoculated and in which the virus was incubated, MDCK cell was selected for incubation of Influenza virus A/PR/8/34 strain (Virus No. 1); HeLa-Y cell was selected for incubation of Newcastle disease virus (NDV) Miyadera strain (Virus No. 2); L-929 cell for incubation of vesicular stomatitis virus (VSV) New Jersey strain (Virus No. 3); HeLa-Y cell for incubation of Vaccinia virus Lister strain (Virus No. 4); and Vero cell for incubation of Herpes simplex virus (HSV) Type 2 196 strain (Virus No. 5).

A compound of this invention as selected for the test from the seven exemplary compounds of this invention, namely the TI-16, TI-27, TI-28, TI-61, TI-62, TI-65 and TI-66 substances was dissolved in dimethylsulfoxide (DMSO) to a concentration of 100 mg/ml, and the resulting solution of the test compound in DMSO was serially diluted with an MEM incubation medium supplemented with 2% CS (calf serum), to prepare test incubation media containing the test compound at graded concentrations.

The test incubation medium so prepared and containing the test compound of this invention was placed in the wells of a 96-wells micro-titer plate (available from Corning Co., U.S.A.), and the test incubation medium was then inoculated with the host cells, followed by incubation of the host cells at 35° C. for 2 days under air containing 5% carbon dioxide gas. After this cell incubation, the host cells were examined under microscope as to whether they had been denatured by the toxic action of the test compound. The above cell-incubation procedure was repeated with the different test incubation media each containing different concentrations of the test compound, so that the minimum concentration (μg/ml) of the test compound which involved the denaturation of the host cells was evaluated.

The above test was repeated also using Amantadine (AM: available as a product Lot No. 122987 from Aldrich Chemical Co. Inc., U.S.A.) or Acyclovir (ACV; available as a product Lot No. UL019 from Nihon Wellcome Company, Japan) as a reference antiviral agent.

The test results obtained are tabulated in Table 2 below.

TABLE 2

| | Cytotoxcity of the tested compounds | | | |
|---|---|---|---|---|
| | Minimum denaturation concentration (μg/ml) of tested compound against | | | |
| Test Compound | HeLa-Y cell | Velo cell | L-929 cell | MDCK cell |
| TI-16 Substance | 250 | 500 | 500 | 1000 |
| TI-27 Substance | 250 | 500 | 250 | 1000 |
| TI-28 Substance | >1000 | >1000 | >1000 | 1000 |
| TI-61 Substance | 125 | 125 | 125 | 250 |
| TI-62 Substance | 250 | 500 | 250 | 1000 |
| TI-65 Substance | 250 | 500 | 250 | 1000 |
| TI-66 Substance | 15.6 | 62.5 | 15.6 | 250 |

TABLE 2-continued

| | Cytotoxicity of the tested compounds | | | |
|---|---|---|---|---|
| | Minimum denaturation concentration (μg/ml) of tested compound against | | | |
| Test Compound | HeLa-Y cell | Velo cell | L-929 cell | MDCK cell |
| Amantadine | — | — | — | 250 |
| Acyclovir | — | >1000 | — | — |

(b) In 96-wells micro-titre plates (available from Corning Co., U.S.A.), the test incubation media containing 2% CS and also the test compound at serially graded concentrations were separately inoculated with the host cells relevantly selected for the respective test viruses, as well as with a test virus at a virus inoculum size of 100 TCID$_{50}$, followed by incubation of the host cells and the test virus at 35° C. for 2 days under air containing 5% carbon dioxide gas. Evaluation was then made of the concentration (μg/ml) of the test compound at which the number of the virus-infested cells that had denatured due to the viral infection as counted by microscopic examination was inhibited to 50% of the total number of the cells. From the evaluated inhibitory concentration (IC$_{50}$; μg/ml) of the test compound which can exert the 50% inhibition of the denaturation of the virus-infested cells, it is clear that the test compound of this invention can inhibit the cytopathic effects of the viruses on the host cell and can exhibit the antiviral activity.

The test results obtained are summarized in Table 3 below.

TABLE 3

| | Antiviral activity of the tested compound | | | | |
|---|---|---|---|---|---|
| | Inhibitory Concentration (IC$_{50}$; μg/ml) of test compound which inhibited by 50% the denaturation of:- | | | | |
| Test Compound | Virus No. 1 -infested MDCK cell | Virus No. 2 -infested HeLa-Y cell | Virus No. 3 -infested L-929 cell | Virus No. 4 -infested HeLa-Y cell | Virus No. 5 -infested Vello cell |
| TI-16 Substance | 375 (2.67) | >250 (<1.0) | >500 (<1.0) | >250 (<1.0) | 375 (1.33) |
| TI-27 Substance | 188 (5.32) | >250 (<1.0) | >500 (<1.0) | >250 (<1.0) | >500 (<1.0) |
| TI-28 Substance | 750 (1.33) | >1000 (—) | 1000 (1.0) | >1000 (—) | >1000 (<1.0) |
| TI-61 Substance | 188 (1.33) | >125 (<1.00) | 93.8 (1.33) | >125 (<1.00) | 93.8 (1.33) |
| TI-62 Substance | >500 (<2.00) | >250 (<1.00) | >125 (<2.00) | >250 (<1.00) | >250 (<2.00) |
| TI-65 Substance | 375 (2.67) | >250 (<1.00) | >125 (<2.00) | >250 (<1.00) | 188 (2.66) |
| TI-66 Substance | >200 (<1.25) | >25 (<0.62) | 18.8 (0.83) | >25 (<0.62) | >100 (<0.63) |
| Amantadine | 50 (5.0) | — | — | — | — |
| Acyclovir | — | — | — | — | 1.17 (>855) |

In Table 3, the numerical figures given in the brackets mean the value of such a quotient of the minimum denaturation concentration of the test compound shown in Table 2, as divided by the IC$_{50}$ value of the test compound shown in Table 3. With increased value of this quotient, the difference of the toxic dose of the test compound from the antivirally effective dose of the test compound increases more advantageously in therapeutic treatment of a virally infested mammalian animal with the test compound.

Test 3

For estimation of toxicity of the new compounds of this invention for mammalian animals, acute toxicity of the TI-27 Substance of Example 1 as a representative example was tested by intraperitoneal administration of a suspension of 25 mg/ml of TI-27 substance in a 0.5% aqueous solution of carboxymethyl cellulose (CMC) to mice (five in each group). The TI-27 substance was given to mice twice a day at a unit dosage of 5 mg, 1.25 mg, 0.313 mg, 0.078 mg or 0.02 mg per mouse for consecutive 4 days, totally 8 times. The number of the surviving mice which tolerated the administration of TI-27 Substance was counted at the 5th day of the tests.

The test results obtained are shown in Table 4 below.

TABLE 4

| Acute toxicity of compound of this invention as given i.p. | |
|---|---|
| Unit dosage (mg/mouse) | Number of surviving mice/number of mice tested |
| 5 | 0/5 |
| 1.25 | 1/5 |
| 0.313 | 5/5 |
| 0.078 | 5/5 |
| 0.02 | 5/5 |

The results of Table 4 show that the compounds of this invention represented by TI-27 Substance are of low toxicity.

EXAMPLE 8

This example demonstrates preparation of tablets containing the compound of this invention.

The TI-16 Substance (100 parts by weight), lactose (200 parts by weight), corn starch (51 parts by weight), and hydroxypropyl cellulose (9 parts by weight) were mixed well and the mixture was granulated by a conventional method. The granules obtained were mixed well with corn starch (8 parts by weight) and magnesium stearate (2 parts by weight) and then compressed

We claim:

1. A compound having the formula (I)

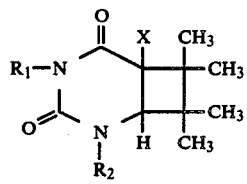

wherein $R_1$ denotes a hydrogen atom, a lower alkyl group or benzyl group and $R_2$ denotes a hydrogen atom, a lower alkyl group or benzyl group and X denotes a hydrogen or fluorine atom; provided that $R_1$ and $R_2$ are simultaneously not hydrogen and that $R_1$ and $R_2$ are simultaneously not methyl group.

2. A compound of claim 1 which is of the formula (Ia)

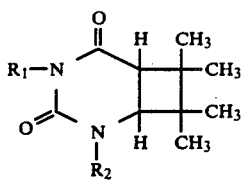

wherein $R_1$ is a hydrogen atom or a lower alkyl group and $R_2$ is a lower alkyl group.

3. A compound of claim 1 which is of the formula (Ib)

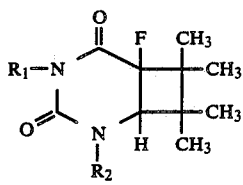

wherein $R_1$ is a hydrogen atom, a lower alkyl group, or benzyl group and $R_2$ is a hydrogen atom, a lower alkyl group, or benzyl group.

4. A compound of claim 2, which is 2,4-diethyl-7,7,8,8-tetramethyl-cis-2,4-diaza-bicyclo[4.2.0]octane-3,5-dione.

5. A compound of claim 3, which is selected from 6-fluoro-4,7,7,8,8-pentamethyl-2,4-diaza-bicyclo[4.2.0]octane-3,5-dione; 2-ethyl-6-fluoro-7,7,8,8-tetramethyl-2,4-diaza-bicyclo[4.2.0]octane-3,5-dione; 2,4-diethyl-6-fluoro-7,7,8,8-tetramethyl-2,4-diaza-bicyclo[4.2.0]octane-3,5-dione; and 2,4-dibenzyl-6-fluoro-7,7,8,8-tetramethyl-2,4-diazabicyclo[4.2.0]octane-3,5-dione.

6. An antiviral composition for the treatment of influenza virus, New Castle disease virus, Vesicular stomatitis virus and Vaccinia virus comprising an effective amount of a compound of the general formula (I) defined in claim 1 as the active ingredient, in association with a pharmaceutically acceptable carrier for the active ingredient.

* * * * *